US005811073A

United States Patent [19]
Kassis et al.

[11] Patent Number: 5,811,073
[45] Date of Patent: Sep. 22, 1998

[54] METHOD FOR RADIOISOTOPIC DETECTION AND LOCALIZATION OF INFLAMMATION IN A HOST

[75] Inventors: Amin I. Kassis, Chestnut Hill; S. James Adelstein, Waban, both of Mass.

[73] Assignee: President and Fellows of Harvard College, Cambridge, Mass.

[21] Appl. No.: 492,425

[22] Filed: Jun. 19, 1995

[51] Int. Cl.$^6$ .......................... A61K 51/00; A61M 36/14
[52] U.S. Cl. ...................... 424/1.73; 424/1.81; 424/1.85
[58] Field of Search ..................... 424/9.1, 1.73, 424/1.11, 1.37, 1.65, 1.81, 1.85, 1.89, 9.3, 9.4, 9.5; 544/294, 264, 242; 514/261, 269

[56] References Cited

U.S. PATENT DOCUMENTS

| | | | |
|---|---|---|---|
| 4,211,773 | 7/1980 | Lopez et al. | 424/1.11 |
| 4,489,052 | 12/1984 | Price | 424/1.11 |
| 4,851,520 | 7/1989 | Kassis et al. | |
| 5,077,034 | 12/1991 | Kassis et al. | 424/1.73 |
| 5,094,835 | 3/1992 | Kassis et al. | 424/1.73 |
| 5,106,837 | 4/1992 | Carson et al. | 514/46 |
| 5,211,937 | 5/1993 | Brandley et al. | 424/1.73 |
| 5,302,384 | 4/1994 | Gimbrone, Jr. et al. | 424/85.2 |
| 5,308,605 | 5/1994 | Kassis et al. | 424/1.73 |
| 5,310,732 | 5/1994 | Carson et al. | 514/46 |
| 5,322,838 | 6/1994 | Silberstein et al. | 514/21 |
| 5,354,751 | 10/1994 | DeGraw et al. | 514/249 |
| 5,376,356 | 12/1994 | Morgan, Jr. | 424/1.69 |
| 5,476,855 | 12/1995 | el Kouni et al. | 514/269 |
| 5,534,535 | 7/1996 | Townsend et al. | 514/394 |

OTHER PUBLICATIONS

Mariani et al. (Apr. 1996), J. Nucl. Med., vol. 37, No. 4, pp. 16S–19S, "Tumor Uptake and Mitotic Activity Pattern of 5–[$^{125}$I] Iodo–2'–deoxyuridine after Intravesial Infusion in Patients with Bladder Cancer".

Annals of the ICRP, vol. 18, No. 1–4, pp. 142 and 263 (Pergamon Press, 1987), entitled: "Radiation Dose to Patients from Radiopharmaceuticals".

Fischman, et al., "Imaging Focal Sites of Bacterial Infection in Rats with Indium–111–Labeled Chemotactic Peptide Analogs," *J. Nucl. Med.*, 1991; 32:483–491, Mar. 1991.

Fischman, et al., "Localization of Fc and Fab Fragments of Nonspecific Polyclonal IgG at Focal Sites of Inflammation," *J. Nucl. Med.* 1990; 31:1199–1205, Jul. 1990.

Palestro, "The Current Role of Gallium Imaging in Infection," *Seminars in Nuclear Medicine*, vol. XXIV, No. 2 (Apr.), 1994, pp. 128–141.

Corstens, et al., "Radioimmunoconjugates in the Detection of Infection and Inflammation," *Seminars in Nuclear Medicine*, vol. XXIII, No. 2 (Apr.), 1993; pp. 148–164.

Kiyosawa, et al., "Orbital Tumor Diagnosis by Positron Emission Tomography Using $^{18}$F–Fluorodeoxyuridine," *Ophthalmic. Res.* 18:292–298 (1986).

*Primary Examiner*—John Kight
*Assistant Examiner*—Dameron Jones
*Attorney, Agent, or Firm*—Fish & Richardson P.C.

[57] ABSTRACT

A method for detecting and localizing the lesions of bacterial and sterile inflammations in a host is disclosed. The method permits in vivo detection and localization of inflammation within 1 to 2 hours of the administration of a radiopharmaceutical agent to the host according to the method of the invention. The radiopharmaceutical agents for use in the method are nucleosides and nucleotides labeled with a radioisotope. The radioisotopes for use in the radiopharmaceutical agents are gamma emitters (preferably halogen gamma emitters) and positron emitters. The radiopharmaceutical agents are administered by parenteral routes, preferably in a pharmaceutically acceptable carrier.

38 Claims, 8 Drawing Sheets

METHOD FOR RADIOISOTOPIC DETECTION AND LOCALIZATION OF INFLAMMATION IN A HOST

STATEMENT AS TO FEDERALLY SPONSORED RESEARCH

The work on which this application is based was supported in part by Grant No. CA15523 from the National Institutes of Health. The government has certain rights to this invention.

BACKGROUND OF THE INVENTION

The invention relates to methods for detection of sterile inflammation as well as inflammation associated with a bacterial infection in a host.

The difficulties inherent in detecting inflammation in patients who present with nonspecific clinical signs of inflammatory disease have sparked efforts to develop effective radiopharmaceutical agents for use in in vivo diagnostic imaging of inflammation. To that end, the diagnostic efficacy of gallium$^{67}$ citrate and radiolabeled carriers such as antibodies, chemotactic peptides and leukocytes in targeting inflammatory lesions has been tested (Fischman et al., *J. Nucl. Med.* 32:483–491, 1991; Corstens and van der Meer, *J. Nucl. Med.* 32:491–493, 1991; McAfee et al., *Semin. Nucl. Med.* 14:83–106, 1984).

SUMMARY OF THE INVENTION

It has been discovered that inflammation in a host animal can be detected in vivo using a deoxyribonucleoside or deoxyribonucleotide labeled with a radioisotope of iodine, bromine, carbon, nitrogen, or oxygen ("radiopharmaceutical agent"). The radiopharmaceutical agent of the invention localizes in both bacterial and sterile inflammatory lesions in as little as an hour after administration, then rapidly clears from blood and tissues of the host. Any inflammatory lesions present in the host are detected by a nuclear imaging technique appropriate to the radioisotope present in the radiopharmaceutical agent: e.g., using a gamma camera, positron emission tomography, positron emission spectography, single photon emission computed tomography, or other suitable detection means.

The method of the invention involves the steps of (a) identifying a mammal (e.g., a human, non-human primate, cow, horse, pig, sheep, goat, rabbit, mouse, rat, guinea pig, hamster, cat, or dog) suspected of having an inflammation; (b) providing the mammal with a diagnostically effective dosage of a radiopharmaceutical consisting of a deoxyribonucleoside or deoxyribonucleotide labeled with a radioisotope of iodine, bromine, carbon, nitrogen, or oxygen; and (c) detecting an accumulation of radioactivity in a site in the mammal, the accumulation being an indication that the inflammation is present in the site.

Gamma emitting radioisotopes preferred for use in the method of the invention include iodine-123, iodine-125, iodine-131, bromine-80m, and bromine-82. Useful positron emitters include halogens such as bromine-75, bromine-76, bromine-77, bromine-80, iodine-122, iodine-124, and iodine-126, as well as non-halogens such as carbon-11, nitrogen-13, oxygen-14 and oxygen-15. The radioisotope is covalently attached to or synthesized as an integral part of a deoxyribo-nucleoside or deoxyribonucleotide. Either purines or pyrimidines can be used. Examples of deoxyribonucleosides are IUdR, BUdR, AdR, CdR, GdR, and TdR (i.e., iodo-uridine, bromo-uridine, adenosine, cytidine, guanidine, and thymidine deoxyribonucleosides, respectively). Also included are deoxyribonucleotides such as the 5' mono-, di-, and triphosphate derivatives of each of the above deoxyribonucleosides.

The radiopharmaceutical agent of the invention is preferably provided in the form of a pharmaceutical composition which includes a diagnostically effective dosage of the agent in a pharmaceutically acceptable carrier suitable for injection into a mammal. It may be supplied in a kit for use in detecting and localizing inflammation in a host, which kit includes (a) a sterile vial containing the radiopharmaceutical agent optionally in a pharmaceutically acceptable carrier; (b) instructions for using the kit; and (c) optionally, a means (such as a syringe) for administering the radiopharmaceutical agent to the host. The dosage is typically between about 0.5 millicuries (mCi) and about 500 mCi; for positron emitters, the preferred dosage is between about 0.5 mCi and about 30 mCi.

Other embodiments and advantages of the invention will become apparent to those of ordinary skill in the art on review of this disclosure.

BRIEF DESCRIPTION OF THE DRAWINGS

FIGS. 5A–5C are scintigraphic images obtained from the animal model described with respect to FIG. 1 at 1 (FIG.

5A), 3 (FIG. 5B) and 24 (FIG. 5C) hours after intravenous injection gallium-67 citrate.

DESCRIPTION OF THE PREFERRED EMBODIMENTS

A. Radiopharmaceutical Agents for Use in the Method of the Invention

The radiopharmaceutical agents of the invention are deoxyribonucleosides or their corresponding deoxyribonucleotides labeled with a radioisotope of iodine, bromine, carbon, nitrogen, or oxygen. Preferably, the labeling is accomplished without use of an intermediate linking molecule, such as the intermediate functional groups which often are used to bind radioisotopes of metallic ions to, for example, immuno-globulins: e.g., bifunctional chelating agents such as diethylenetriaminepentacetic acid (DTPA) and ethylenediaminetetraacetic acid (EDTA).

Nucleosides useful in the invention include IUdR, BUdR, TdR, CdR, AdR, and GdR. Such nucleosides, and their corresponding 5'mono-, di-, and triphosphophate derivatives, may be purchased from commercial sources or synthesized by well-known techniques, as described, for example, in Bergstrom, et al., J. Carbohyd., "Nucleosides and Nucleotides", 4:257–269, 1977, the disclosure of which is incorporated herein to illustrate knowledge in the art concerning synthesis of nucleosides and nucleotides. Any of the deoxynucleosides or deoxynucleotides used in the claimed method can be labelled in one or more sites with an isotope of carbon, nitrogen, or oxygen (e.g., carbon-11, nitrogen-13, oxygen-14, or oxygen-15). Certain of the deoxynucleosides and deoxynucleotides alternatively can be labelled with an isotope of a halogen. For example, IUdR (or the corresponding nucleotide) can be labelled with any isotope of iodine (e.g., iodine-122, iodine-123, iodine-124, iodine-125, iodine-126, or iodine-131), while BUdR (or the corresponding nucleotide) can be labelled with any isotope of bromine (e.g., bromine-75, bromine-76, bromine-77, bromine-80, bromine-80m, or bromine-82).

For purposes of comparing these carriers to those of the prior art, the rate and extent of localization in inflammatory lesions of both the radiopharmaceutical agents of the invention and gallium-67 citrate was tested in animal models of sterile and bacterial inflammation. The labeled nucleosides and nucleotides of the invention were determined to be superior to the commonly used gallium-67 agent for obtaining rapid images of both infectious and sterile inflammatory lesions.

Figure 1:
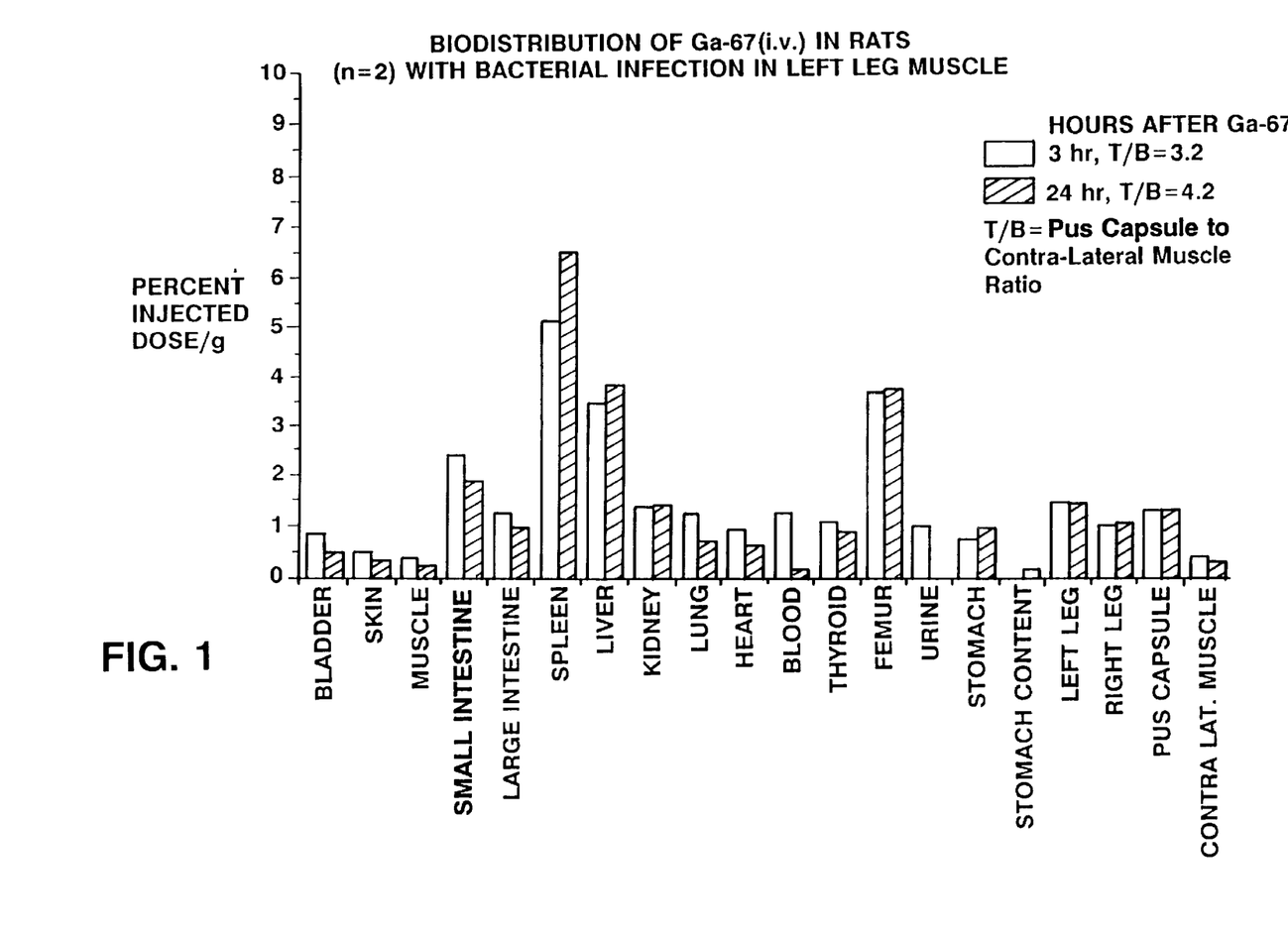
FIG. 1 is a bar graph showing the biodistribution of gallium-67 citrate after intravenous injection into rats after induction of a bacterial infection in the left hind leg muscle. Biodistribution is measured as a function of the percentage of the injected dose of radioisotope/gram of biopsy sample weight. The white bars indicate distribution at 3 hours, while the cross-hatched bars indicate distribution at 24 hours. "n" indicates the number of animals tested. "T/B" indicates the ratio of radioactivity detected in target (inflamed) tissues to radioactivity detected in background tissue.
Figure 2:
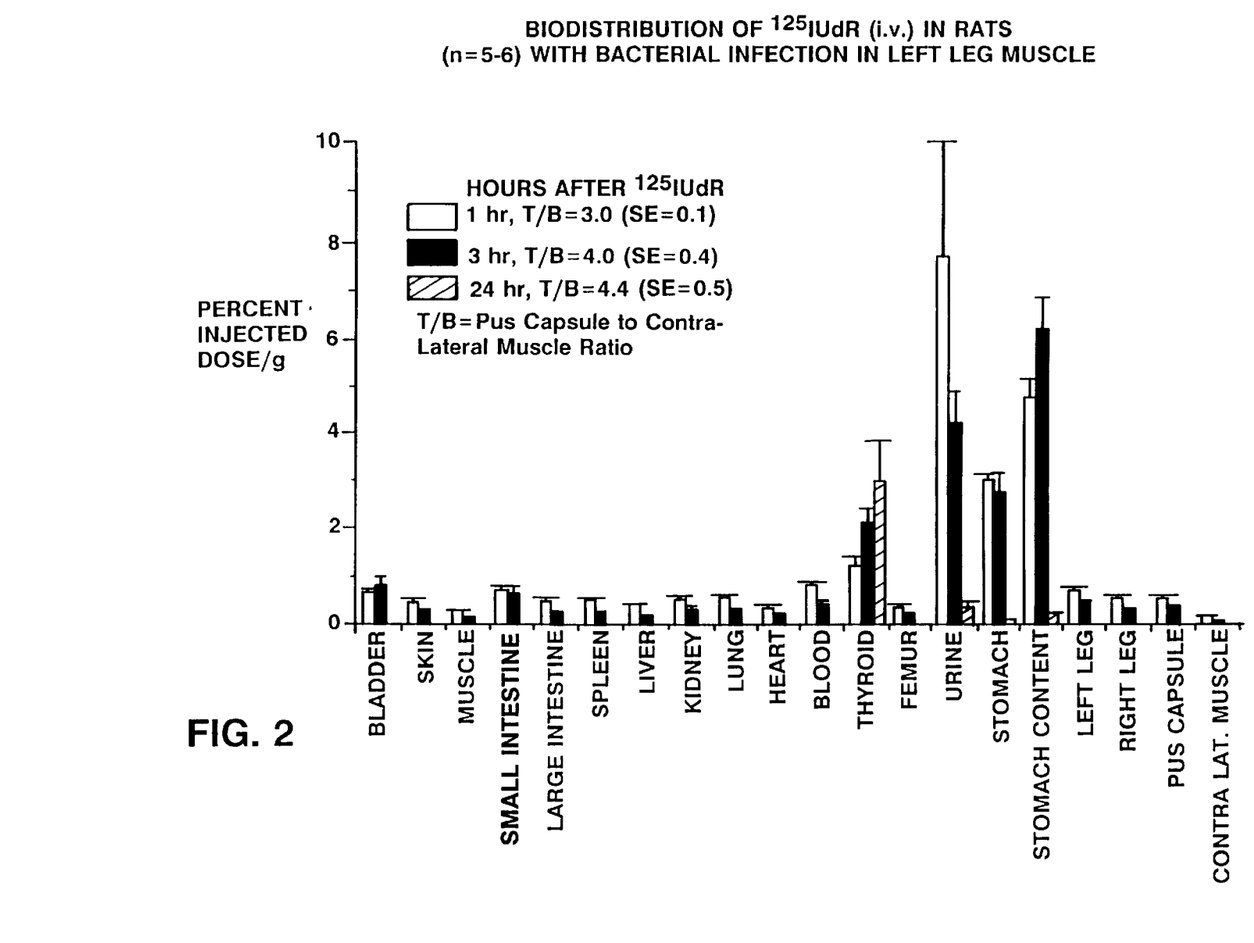
FIG. 2 is a bar graph showing the biodistribution of $^{125}$I labeled deoxyuridine after intravenous injection into rats after induction of a bacterial infection in the left hind leg muscle. Biodistribution is measured as a function of the percentage of the injected dose of radioisotope/gram of biopsy sample weight. The white bars indicate distribution at 1 hour, the solid bars indicate distribution at 3 hours and the cross-hatched bars indicate distribution at 24 hours. "n" indicates the number of animals tested. "T/B" indicates the ratio of radioactivity detected in target (inflamed) tissues to radioactivity acted in background tissue.
Figure 3:
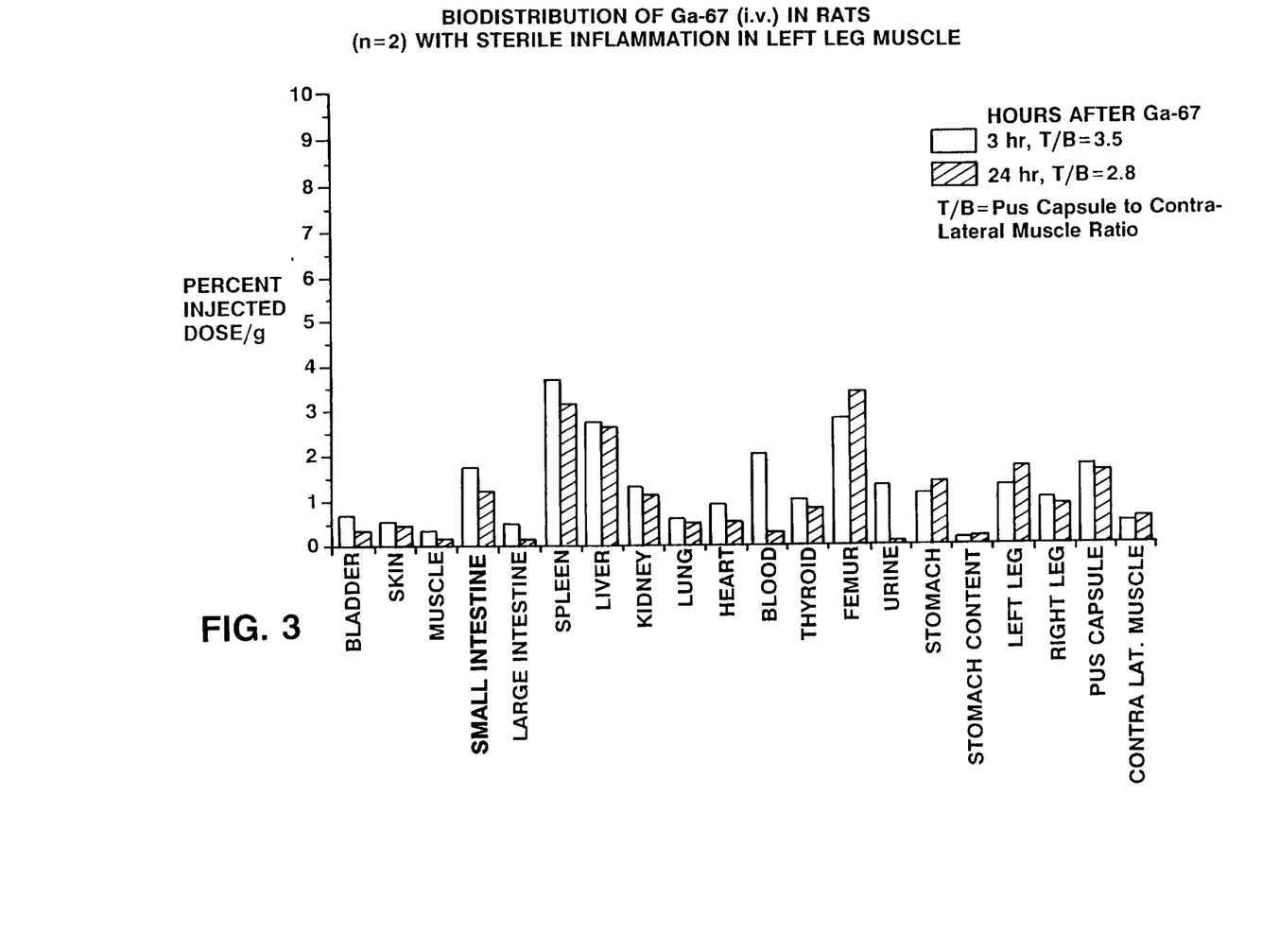
FIG. 3 is a bar graph showing the biodistribution of gallium-67 citrate after intravenous injection into rats after induction of sterile inflammation in the left hind leg muscle. Biodistribution is measured as a function of the percentage of the injected dose of radioisotope/gram of biopsy sample weight. The white bars indicate distribution at 3 hours and the cross-hatched bars indicate distribution at 24 hours. "n" indicates the number of animals tested. "T/B" indicates the ratio of radioactivity detected in target (inflamed) tissues to radioactivity detected in background tissue.
Figure 4:
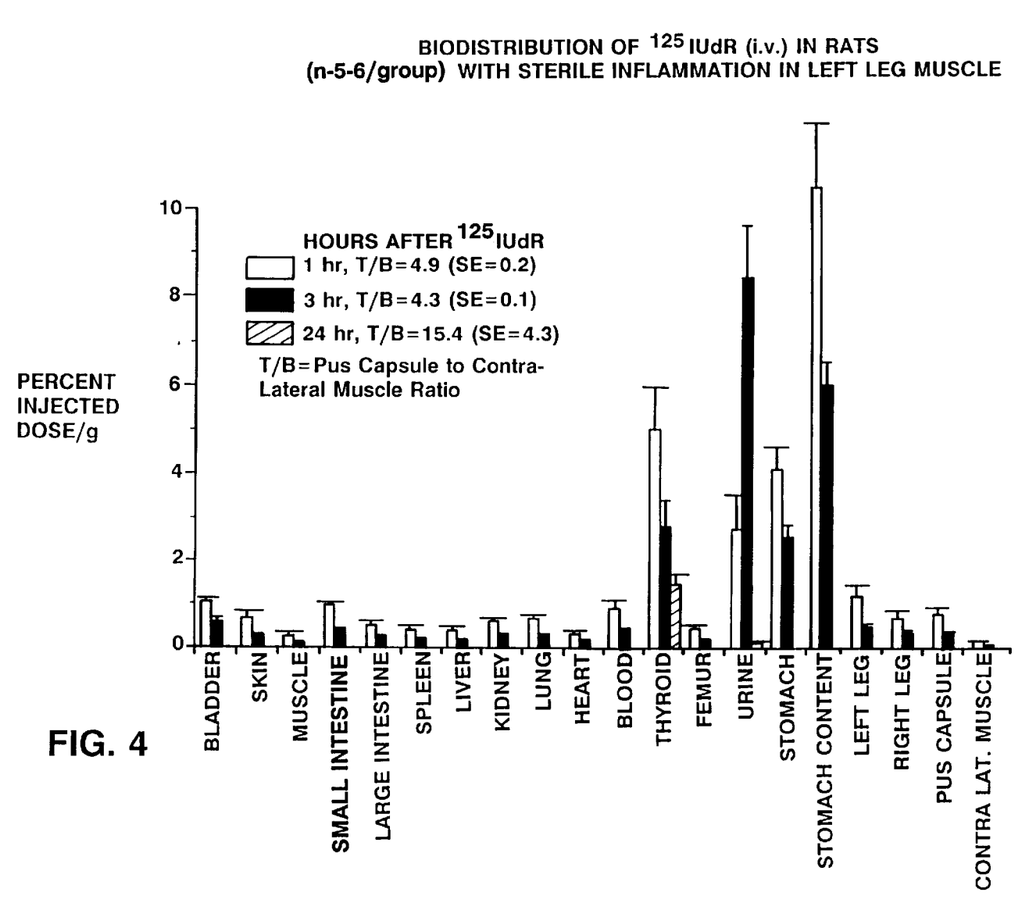
FIG. 4 is a bar graph showing the biodistribution of $^{125}$I labeled deoxyuridine after intravenous injection into rats after induction of sterile inflammation in the left hind leg muscle. Biodistribution is measured as a function of the percentage of the injected dose of radioisotope/gram of biopsy sample weight. The white bars indicate distribution at 1 hour, the solid bars indicate distribution at 3 hours, and the cross-hatched bars indicate distribution at 24 hours. "n" indicates the number of animals tested. "T/B" indicates the ratio of radioactivity detected in target (inflamed) tissues to radioactivity detected in background tissue.
Figure 5A:
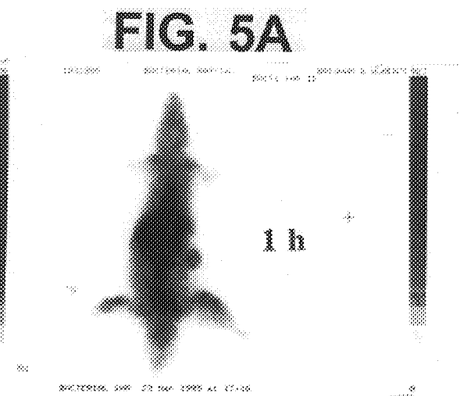
Figure 5B:
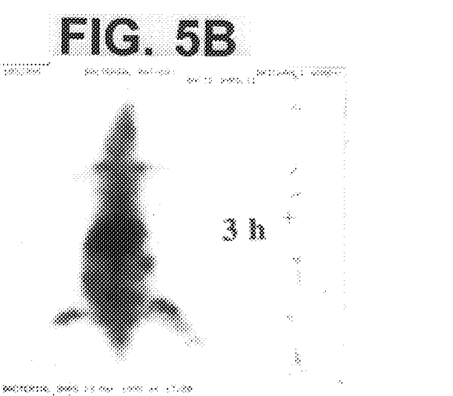
Figure 5C:
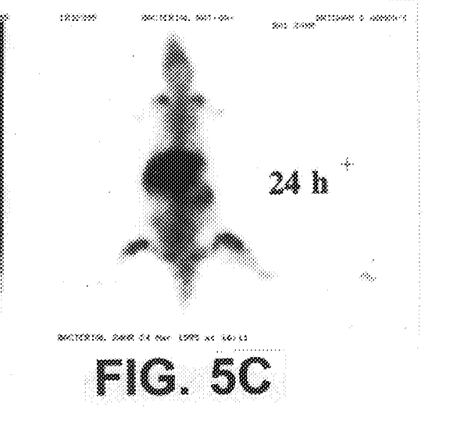
Figure 6A:
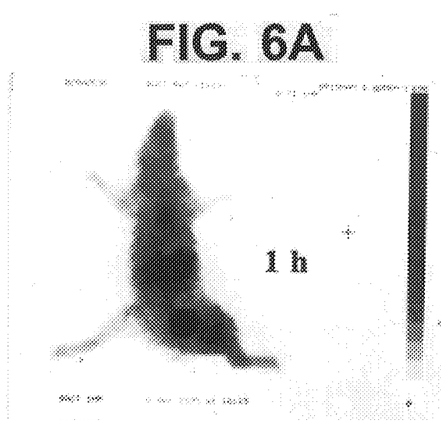
FIGS. 6A–6C are scintigraphic images obtained from the animal model described with respect to FIG. 2 at 1 (FIG. 6A), 3 (FIG. 6B) and 24 (FIG. 6C) hours after intravenous injection of the radiopharmaceutical. $^{123}$I-labeled deoxyuridine was used as the radiopharmaceutical agent, instead of $^{125}$I- labeled deoxyuridine.
Figure 6B:
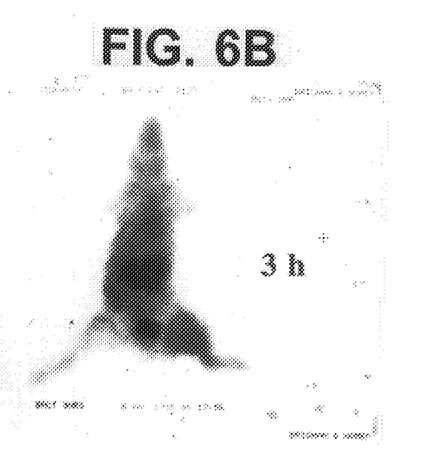
Figure 6C:
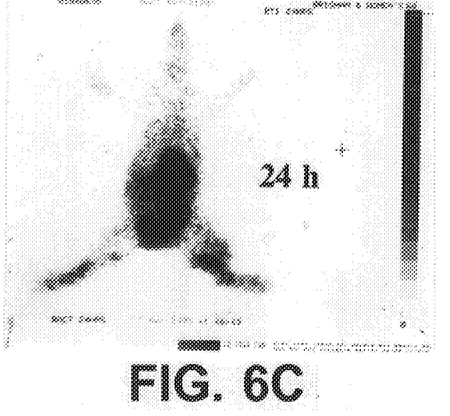
Figure 7A:
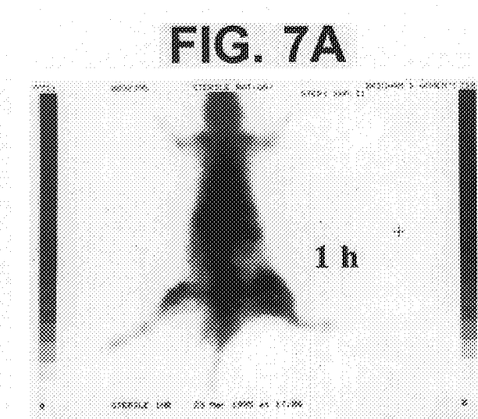
FIGS. 7A–7C are scintigraphic images obtained from the animal model described with respect to FIG. 3 at 1 (FIG. 7A), 3 (FIG. 7B) and 24 (FIG. 7C) hours after intravenous injection of the gallium-67 citrate.
Figure 7B:
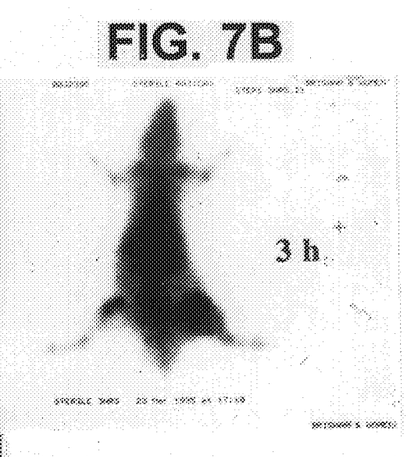
Figure 7C:
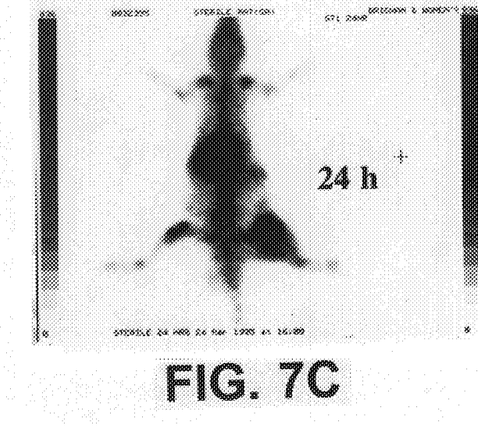
Figure 8A:
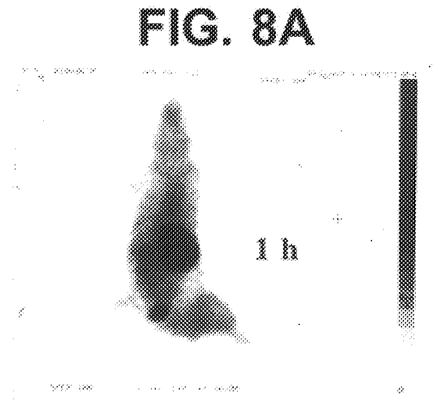
FIGS. 8A–8C are scintigraphic images obtained from the animal model described with respect to FIG. 4 at 1 (FIG. 8A), 3 (FIG. 8B) and 24 (FIG. 8C) hours after intravenous injection of the radiopharmaceutical. $^{123}$I-labeled deoxyuridine was used as the radiopharmaceutical agent of the experiment instead of $^{125}$I-labeled deoxyuridine.
Figure 8B:
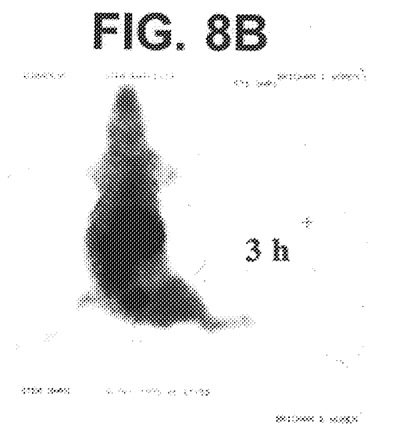
Figure 8C:
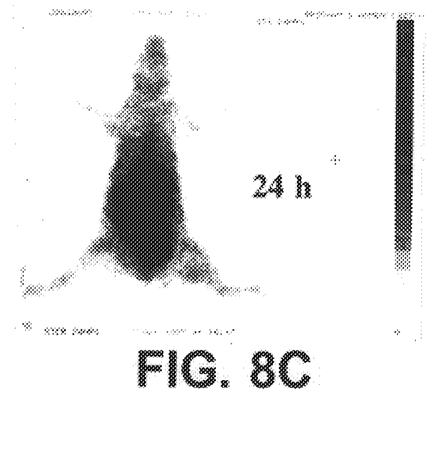

In particular, as shown in FIGS. 2 and 6, $^{125}$IUdR accumulated in target (inflamed) tissues of rats suffering from an inflammatory bacterial infection as early as 1 hour following their administration. In other rats suffering from the same condition, gallium-67 citrate did not accumulate at the site of inflammation until several hours after its administration (FIGS. 1 and 5). As shown in FIGS. 4 and 8, a second radiolabeled nucleoside, $^{123}$IUdR, also accumulated in target (inflamed) tissues of rats with sterile inflammatory lesions more quickly than did gallium-67 citrate (FIGS. 3 and 7). The relative extent of accumulation of the radiopharmaceutical agents of the invention in target versus background tissues was determined to be adequate to enable images of inflammatory lesions to be distinguished from adjacent background tissues.

In selecting a radioisotope for use as a label for in vivo diagnostic imaging, the type of detection instrument available must be considered. The radioisotope chosen must have a type of decay which is detectable by a given type of instrument. Still another important factor in selecting a radioactive label for in vivo diagnosis is that the half-life of the molecule must be long enough so that it is still detectable at the time of maximum uptake by the target, but short enough so that deleterious radiation with respect to the host is minimized. Ideally, a radioisotope used for in vivo imaging will produce a large number of photons in the 140–250 keV range, which may be readily detected by conventional nuclear imaging cameras. Further, the radioisotopes used to label the nucleosides or nucleotides of the invention will preferably be those which will not interfere with cellular incorporation of the nucleosides or nucleotides and which will retain the capacity for detectable decay despite such incorporation.

Types of radioisotopes which meet the aforementioned criteria for use in the method of the invention are those which emit gamma or positron radiation (hereafter, "gamma emitters" and "positron emitters"). A simple method for synthesizing radiolabeled nucleosides and nucleotides is disclosed in Kassis et al., U.S. Pat. No. 4,851,520 (the +520 patent), which disclosure is herein incorporated by reference to illustrate known methods for synthesis of such molecules suitable for use in the method of the invention.

Briefly, according to the +520 patent, radioiodinated pyrimidine nucleosides and nucleotides are prepared by contacting a water-soluble halomercuri-pyrimidine nucleoside or nucleotide with an aqueous medium containing a dissolved radioactive iodide ion and an oxidizing agent. The molar concentration of nucleoside or nucleotide in the reaction process exceeds that of the iodide. The radioiodinated product of the reaction is separated from residual halomercuri-pyrimidine by conventional filtration procedures. The technique is useful in preparing any nucleoside or nucleotide labeled with a radioactive halogen.

Those of ordinary skill in the art will be familiar with, or can readily ascertain, other synthesis methods appropriate to the preparation of radiopharmaceutical agents for use in the inventive method. For example, other suitable radioiodination labeling techniques are taught in Keough et al., J. Labeled Compound Radiopharm. 14:83–90, 1978. Techniques for labeling with non-halogen radioisotopes (such as $C^{11}$) are also well-known and include the technique referred to in Kubota et al., Jpn. J. Cancer Res. 80:778–782, 1989.

For in vivo administration, the radiopharmaceutical agents will preferably be formulated in a pharmaceutically acceptable carrier, most preferably a liquid (see, standard reference Remington's Pharmaceutical Sciences, which is incorporated herein by reference to illustrate knowledge in the art concerning suitable pharmaceutical carriers). Exemplary liquid carriers are saline, Ringer's solution, syrup, peanut oil, olive oil and like emulsions. The formulation can be in the form of an aqueous or nonaqueous liquid suspension and may include pharmaceutically acceptable preservatives.

The materials for use in the method of the invention are ideally suited for the preparation of a diagnostic kit. Kits useful in the claimed method comprise container means (such as vials, tubes, bottles, and the like) as well as means (such as a sterile syringe) for administering the contents of the container to a host. The syringe may be provided already loaded with a single dose of the radiopharmaceutical agent, or the agent and/or a pharmaceutically acceptable carrier may be provided mixed or separated in one or more containers. Appropriate instructions regarding the safe use of the radiopharmaceutical agents of the invention will be provided on the container labels or in a separate instruction sheet.

B. Detection of Radioactivity at Inflammatory Lesions According to the Invention The radiopharmaceutical agents of the invention may be used to detect and localize both sterile and bacterial inflammations. The method of the invention is particularly advantageous in that it permits detection of acute inflammations and provides diagnostic results within 1 to 2 hours of the administration of the radiopharmaceutical agent to the host. Further, the radiopharmaceutical agents of the invention can be expected to provide diagnostically sufficient images of inflammation for several hours, thus permitting detection of inflammation during the course of treatment.

Those of ordinary skill in the art will be familiar with, or can readily ascertain the identity of, techniques and instruments for in vivo detection of radioactivity provided in the host by the radiopharmaceutical agents used according to the invention. To detect radioactivity produced by gamma emitter radiopharmaceutical agents, an instrument commonly known as a gamma camera (i.e., a system of scintillation crystals or photo multiplier tubes for analysis of radioactive decay) will be used to detect gamma emission from the radiopharmaceutical agent. Alternatively, single photon emission computed tomography (SPECT) can be used. To detect radioactivity produced by positron emitter radiopharmaceutical agents, techniques and instruments for positron emission tomography (PET) are available to, and well-known in, the art. The selection of a radiopharmaceutical agent and detection technique suitable for a given application is within the ordinary level of skill in the art. Factors to be considered in this respect include the existence of any host sensitivity to a particular radioisotope, in vivo toxicity and efficiency of such molecules, potential pharmaceutical interactions between the radiopharmaceutical agent and other medications taken by the host, the availability of particular detection instruments, and cost of materials.

For diagnostic purposes, the radiopharmaceutical agent is administered to the host in a dose which is diagnostically effective for the purpose. The term "diagnostically effective" means that the radiopharmaceutical agent is administered in sufficient quantity to enable detection of any significant inflammatory lesions present in the host. In general, the concentration of radiopharmaceutical agent to be administered should be chosen such that its accumulation in inflammatory lesions is detectable compared to the background. Further, it is desirable that the radiopharmaceutical agent be rapidly cleared from the circulatory system in order to give the best target-to-background signal ratio.

In considering dosages of radiopharmaceutical agents to be administered, those of ordinary skill in the art will appreciate that it is not known exactly why certain radiopharmaceutical agents display a preference for accumulation at inflammatory lesions in vivo. It has been hypothesized that phagocytosis plays a role or that the agents accumulate in the extracellular spaces of tissues as a result of increased permeability of veins at the site of inflammation. Also, although the invention is not limited by any particular theory regarding why nucleosides and nucleotides will target inflammatory lesions in vivo, it is likely that they are incorporated into the nuclei of proliferating cells, such as bacteria at the site of an infection. Whatever the physiologic mechanisms at work, the need to provide a concentration of radiopharmaceutical agent sufficient to concentrate in target tissues will be taken into account.

The dosage of radiopharmaceutical agent required to detect inflammation in a host will vary with the radioactivity of the radioisotope present in the agent. For example, the mean lethal dosages of both $^{125}$I and $^{123}$I have been calculated at about 79 ±/–9 cGy (in Chinese hamster ovary cells; see, e.g., Makrigiorgos et al., *Radiat. Res.* 118:532–544). For diagnostic purposes, the dosage will of course be substantially less than the mean lethal dose for the radioisotope. Because of the nature of gamma and positron emissions, the dosages of gamma emitters required by the invention will be less than the dosages of positron emitters required by the invention. The half-life of the radioisotope will also be taken into account, with a shorter half life meaning that a larger dose of radioactivity can be administered safely. For example, the half-life of 123I is about 13 hours, while that of $^{131}$I is about 8 days and that of $^{11}$C is only 20 minutes. One of ordinary skill in nuclear medicine would know to take the above and other salient characteristics of the radioisotopes into account when calculating an appropriate dosage. As a general matter, it is expected that a useful dose of the radiopharmaceutical would deliver between about 0.5 and about 500 millicuries (mCi). Where the radiopharmaceutical is a positron-emitter, the diagnostically effective dosage would be approximately 0.5 mCi to 30 mCi. It is expected that a useful dose of $^{123}$I-labelled deoxyribonucleoside or deoxyribonucleotide would be between 1 and 20 mCi, while less than 5 mCi of the longer-lived $^{131}$I would be used (e.g. 0.5–5 mCi). Approximately 200 mCi $^{11}$C can be used (e.g., 100–300 mCi). In general, these dosage ranges will not vary substantially with the weight, age and sex of the host. However, in juvenile hosts, dosages in the lower spectrum of each preferred dosage range will be preferred, in order to limit accumulation of radioactivity in dividing cells.

Selection and modification of particular doses for each radiopharmaceutical agent to be used in the invention is within the ordinary level of skill in the art. In particular, dosimetry calculations are well-known in the art which permit estimation of the distribution and radioactive burden to host tissues and cells on administration of radioisotopes. For review in this regard, those of skill in the art may wish to consult Makrigiorgos et al., *J. Nucl. Med.* 31:1358–1363, 1990, the disclosure of which is incorporated herein by reference to illustrate knowledge in the art concerning dosimetric calculations of radioactivity distribution. Suitable animal models for use in evaluating the characteristics and efficacy of particular pharmaceutical agents are described in Example 1 and Example 2.

The radiopharmaceutical agents of the invention will be administered by a parenteral route selected to target the suspected site of inflammation. For most indications, the preferred route of administration will be by intravenous injection. However, intra-arterial, intrathecal, and intraperitoneal routes may also be preferred for targeted access to certain organs, such as the heart.

For monitoring the course of an inflammatory condition in the host, as well as the host's responsiveness to therapy, the site of inflammation may be imaged according to the invention more than once. Clearance of any previously administered radioactive agents (including those of the invention and chemotherapeutic agents) should be considered to limit detection of residual radioactivity. Rates of clearance may be determined based on known clearance rates for the particular radioisotopes present, or may be inferred by reimaging the host prior to readministering a radiopharmaceutical agent according to the invention. Accumulation of the radiopharmaceutical agents of the invention in background will also be taken into account in this regard to maximize the target-to-background radioactivity ratios achieved in each imaging session.

Protocols and formulas for use in determining target-to-background ratios for radioactivity are well-known in the art and are exemplified below. Certain radiopharmaceutical agents may accumulate in tissues adjacent to or distant from target tissues. Where possible, radiopharmaceutical agents will be chosen which do not accumulate at high levels in background tissues adjacent to suspected or known lesions of inflammation (as compared to accumulation of the agent in more distant background tissues).

Examples illustrating practice of the method of the invention are set forth below. These examples should not, however, be considered to limit the scope of the invention, which is defined by the appended claims. In the examples, the abbreviation "min." refers to minutes, "hrs" and "h" refer to hours, "i.v." and "i.p." respectively refer to intravenous and intraperitoneal, and measurement units (such as "ml") are referred to by standard abbreviations.

EXAMPLE 1

Animal Model of Sterile Inflammation

Male Sprague-Dawley rats weighing between 150–200g were obtained from the Charles River Breeding Laboratories in Burlington, Mass. To block thyroidal uptake of radioiodine, the drinking water of the rats was charged with a 0.1% KI solution in water two days before injecting the radiopharmaceutical. To anaesthetize the animals during testing, ketamine (40 mg/kg) and xylazine (10 mg/kg) were administered intra peritoneally (1.0 ml/kg) prior to surgical procedures. For the imaging studies, each animal received 1.5 ml/kg of a mixture of ketamine (75 mg/kg), xylazine (39 mg/kg) and acepromazine (0.75 mg/kg).

To induce a localized sterile inflammation, 0.1 ml of turpentine oil (Rectified Turpentine Oil for medical use, Gentry Corporation, Fair Lawn, N.J.) was injected into the left thigh muscle of anesthetized rats. In this model, the maximum target to background tissue ratio for image intensity for both sterile and bacterial inflammation has been previously observed at 3 hrs following delivery by i.v. injection (0.25 mg/kg) of 200–300 $\mu$Ci gallium-67 citrate (DuPont) or 300–500 $\mu$Ci $^{99m}$Tc-human serum albumin (Medi-Physic, Richmond, Calif.) and at 24 hrs after 100–150 $\mu$Ci of $^{111}$In-IgG or $^{125}$I-IgG.

EXAMPLE 2

Animal Model of Bacterial Inflammation

A frozen sample of E. coli bacteria (clinical isolate; ATCC 9339) was used to inoculate a 10 ml trypticase soy medium (trypticase soy broth, BBL #11768, 30 g/L water), and the tube was incubated overnight at 37% C. This culture was used to grow single colonies by streaking the sample on agar plates (100 mm petri dishes each containing 15 ml of 0.15% agar-gel in the same medium). Good colonies develop in 10–11 hours at 37° C. The agar plates containing bacterial colonies were stored upside down at 4° C. A single colony of bacteria from the agar plate was used to inoculate 10 ml trypticase soy medium, and the tube was incubated overnight at 37° C. with vigorous shaking. Two ml of this overnight culture was transferred into 100 ml trypticase soy medium and the sample incubated at 37° C. with vigorous shaking until the culture reached an $OD_{600}$ of ~0.8 (in about 2 hrs). This 100 ml culture contained ~$6.4 \times 10^{10}$ bacterial cells (1 $OD_{600}$=$8 \times 10^8$ cells/ml).

The culture was centrifuged at 5500 rpm for 5 min at 4° C. in a Sorvall SS-34 rotor, the bacterial pellet resuspended in saline to give ~$2.5 \times 10^9$ bacteria/ml, and 0.1 ml of resuspended cells injected into the left thigh muscle of each anesthetized rat.

EXAMPLE 3

Detection and Localization of Sterile and Bacterial Inflammation in Rats: Biodistribution of I.V. Injected Radiopharmaceuticals No-carrier added radioiodinated deoxyuridine ($^{125}$IUdR) was synthesized by the method described in the above disclosure. Commercially available gallium-67 citrate of known biodistribution characteristics was obtained, for comparison to $^{125}$IUdR. 24 hrs after each rat described in Example 2 received an intramuscular injection of E. coli or after each rat described in Example 1 received an intramuscular injection of turpentine oil (to permit comparison of activity in a bacterial inflammation lesions to activity in a sterile inflammation lesions) in the left rear thigh, each rat received either $^{125}$IUdR (about 5 $\mu$Ci/rat) or gallium-67 citrate (about 10 $\mu$Ci/rat) suspended in 0.1 ml saline, by injection into the tail vein.

At one, three and 24 hrs after $^{125}$IUdR or gallium-67 citrate administration, the animals from each group were anesthetized, blood collected via cardiac puncture, urine aspirated from the urinary bladder, and the rats humanely sacrificed. The biodistribution of each radiopharmaceutical (measured as a function of the % injected dose/gram body weight) was then determined in various normal tissues and organs, as well as the left and right legs, the pus capsule formed within the leg and in contralateral muscle tissues (i.e., background tissues unaffected by inflammation) of equivalent weight.

To determine the distribution of each radiopharmaceutical in various tissues of each rat (i.e., the "biodistribution" of each radiopharmaceutical), samples of background tissues and organs (blood, lung, liver, spleen, kidney, muscle and intestine), of target tissue (the pus capsule formed in the leg) and of contralateral muscle tissue (background tissue adjacent to target tissue) were obtained from each rat and weighed. Radioactivity in each sample was measured in a well-type gamma counter (from LKB, Wallac Oy, Finland). To correct for radioactive decay and permit calculation of activity in each organ or tissue as a fraction of the injected dosage of radiopharmaceutical, aliquots of the injected doses were counted at the same time that radioactivity in each sample was determined. The results were measured as a function of the percentage of injected dose/gram (% ID/g). For further reference regarding measurements of biodistribution of radiopharmaceuticals, particularly in blood, those of ordinary skill in the art may wish to refer to Baker et al., "*The Laboratory Rat*" (Acad.Press N.Y., 1980).

The data obtained demonstrate that both $^{125}$IUdR and gallium-67 citrate concentrate within both bacterial (*E. coli*) inflammatory lesions (pus capsule) and sterile inflammatory lesions (turpentine oil) to a greater extent than in the contralateral tissues (see Tables 1 and 2 below) and most of the normal organs and tissues (see FIGS. 1–4). Thus, $^{125}$IUdR accumulates in both sterile and bacterial inflammatory lesions in preference to unaffected background tissues, even those adjacent to the lesion.

More specifically, pus capsule to contralateral tissue (T/B) ratios calculated from biodistribution data in rats with sterile inflammation and injected with $^{67}$Ga or $^{125}$IUdR (Table 1) clearly demonstrate that radiolabeled IUdR is much better than $^{67}$Ga for the radioscintigraphic detection of these lesions at both time periods (3 h and 24 h) for which a comparison can be made.

TABLE 1

Pus Capsule and Contralateral Tissue (T/B) Ratios
(mean +SD) in Rats with Sterile Inflammation
Following i.v. Injection of gallium-67 citrate or $^{125}$IUdR
--Biodistribution--

|  | n* | 1 h | 3 h | 24 h |
|---|---|---|---|---|
| $^{67}$Ga | 2 | — | 3.55 ± 0.24 | 2.85 ± 0.64 |
| $^{125}$IUdR | 6 | 4.93 ± 0.46 | 4.32 ± 0.13 | 15.44 ± 4.23 |
|  |  | (n = 3) |  |  |

Injected dose (ID): 10 μCi/rat $^{67}$Ga;
5 μCi/rat $^{125}$IUdR; i.v.
Injection volume: 0.1 ml
Data Analysis Equation: T/B Ratio = $A_t/A_b$
Where $A_t$ = %ID/g in pus capsule
$A_b$ = %ID/g over contralateral muscle

*n = number of animals

Further, pus capsule to contralateral tissue (T/B) ratios calculated from biodistribution data in rats with bacterial infection and injected with $^{67}$Ga or $^{125}$IUdR (Table 2) demonstrate that radiolabeled IUdR is better for the radioscintigraphic detection of these lesions at all the three time periods (1 h, 3 h, and 24 h).

TABLE 2

Pus Capsule and Contralateral Tissue (T/B) Ratios (mean ±SD)
in Rats with Bacterial Infection
Following i.v. Injection of Gallium-67 Citrate or $^{125}$IUdR
--Biodistribution--

|  | n* | 1 h | 3 h | 24 h |
|---|---|---|---|---|
| $^{67}$Ga | 2 | — | 3.21 ± 0.13 | 4.07 ± 1.09 |
| $^{125}$IUdR | 5 | 3.02 ± 0.14 | 4.03 ± 0.37 | 4.44 ± 0.47 |
|  |  | (n = 3) |  |  |

Injected dose: 10 μCi/rat $^{67}$Ga;
5 μCi/rat $^{125}$IUdR; i.v.
Injection volume: 0.1 ml
Data Analysis Equation.: T/B Ratio = $A_t/A_b$
Where $A_t$ = %ID/g in pus capsule
$A_b$ = %ID/g over contralateral muscle

*n = number of animals

EXAMPLE 4

Detection and Localization of Sterile and Bacterial Inflammation in Rats: Radiomaging of Inflammatory Lesions A further set of rats prepared as described in Examples 1 and 2 received intravenous injections of either $^{123}$IUdR (at a dose of about 1.5 mCi/rat) or gallium-67 citrate (at a dose of about 0.2 mCi/rat). After 1, 3 and 24 hours, rats from each group were anesthetized and imaged using a gamma camera (the General Electric STARCAM™ 400 fitted with parallel hole medium collimator). Anterior images were obtained $10^6$ counts/frame except for the 24 h period for $^{123}$IUdR where a 15 min scan was carried out. A 20% window was present over the 159 keV photopeaks of $^{67}$Ga (93 kev, 184 keV, and 298 keV).

Regions of interest (ROI) were drawn over the inflamed areas (3×4 pixel) and over the contralateral area in each rat. Total counts in these regions were used to calculate Target to Background (T/B) ratios and to calculate Figure of Merit (FOM; statistical significance) values using either of the following equations:

$$FOM = (A_t - A_b)^2 / (A_t + A_b) \tag{1}$$

or $$FOM = (A_t - A_b) / A_b \tag{2}$$

Where $A_t$ = counts in ROI (3×4) over pus capsule; and $A_b$ = counts in ROI (3×4) over contralateral muscle.

Equation (1) is derived from the Report of the National Council on Radiation Protection and Measurements, Nuclear Medicine, "*Factors Influencing the Choice and Use of Radionuclides in Diagnosis and Therapy*", Report No. 70, p.79 (NRCP, Bethesda, Md., 1982). Equation (2) is derived from Rubin et al., *J. Nucl. Med.* 30:385–389, 1989. For purposes of reference, the disclosures of each of these publications is incorporated herein.

Scintigraphic images (FIGS. 5–8) obtained in animals with bacterial infection or sterile inflammation in the left thigh muscle 1, 3, and 24 h after intravenous injection of gallium-67 citrate or $^{123}$IUdR demonstrate that both agents can clearly detect the lesion in the left leg.

As shown in the Tables below, the data obtained from these experiments also show that:

1. FOM values calculated from imaging of rats with sterile inflammation and injected with gallium-67 citrate or $^{123}$IUdR (Table 3) demonstrate that $^{123}$IUdR is the superior agent for early (i.e. 1 h) radioscintigraphic detection of these lesions while gallium-67 citrate produces equal or higher FOM values at later time points (3 hrs and 24 hrs):

TABLE 3

Figure of Merit (FOM) (mean ±SD) in
Rats with Sterile Inflammation Following
i.v. Injection of $^{67}$Ga-citrate or $^{123}$IUdR
--Gamma Camera Imaging--

|  | n | 1 h | 3 h | 24 h |
|---|---|---|---|---|
| $^{67}$Ga | 4 | 1037 ± 215 | 1581 ± 143 | 1958 ± 149 |
| $^{123}$IUdR | 4 | 14444 ± 559 | 750 + 268 | 69 + 52 |

Injected dose: 0.2 mCi $^{67}$Ga-citrate;
1.5 mCi/rat $^{123}$IUdR; i.v.
Injection volume: 0.1 ml
Data Analysis Equation: (1)

| $^{67}$Ga | 4 | 1.75 ± 0.2 | 2.61 ± 0.18 | 4.09 ± 0.50 |
| $^{123}$IUdR | 4 | 3.13 ± 0.53 | 2.33 ± 0.46 | 2.07 ± 1.46 |

Data Analysis Equation: (2)

2. FOM values calculated from imaging of rats with bacterial infection and injected with gallium-67 or $^{123}$IUdR (Table 4) demonstrate that the latter is the superior agent for radioscintographic detection of such lesions at all three time periods tested (1 h, 3 hrs and 24 hrs):

TABLE 4

Figure of Merit (FOM) (mean + SD) in
Rats with Bacterial Infection Following
i.v. Injection of $^{67}$Ga-citrate or $^{123}$IUdR
--Gamma Camera Imaging--

|  | n | 1 h | 3 h | 24 h |
|---|---|---|---|---|
| $^{67}$Ga | 3 | 49 ± 60 | 306 ± 210 | 231 ± 135 |
| $^{123}$IUdR | 4 | 1770 ± 598 | 1507 ± 775 | 214 + 135 |

Injected dose: 0.2 mCi $^{67}$Ga-citrate;
1.5 mCi/rat $^{123}$IUdR; i.v.
Injection volume: 0.1 ml
Data Analysis Equation: (1)

| $^{67}$Ga | 3 | 0.26 ± 0.11 | 1.01 ± 0.29 | 0.90 ± 0.21 |
| $^{123}$IUdR | 4 | 2.72 ± 0.53 | 2.53 ± 0.40 | 4.35 ± 1.19 |

Data Analysis Equation: (2)

3. Pus capsule to contralateral tissue (T/B) ratios calculated from imaging of rats with sterile inflammation and injected with gallium-67 citrate or 123IUdR (Table 5) demonstrate that the latter is superior to gallium-67 for obtaining early (i.e., 1 h) radioscintigraphic detection of these lesions. Using this T/B parameter, the efficacy of the two radiopharmaceuticals is equal at 3 hrs. However, by 24 hrs., gallium-67 citrate produces higher T/B ratios:

TABLE 5

Pus Capsule to Contralateral Tissue (T/B)
Ratios (mean ±SD) in Rats with Sterile
Inflammation Following i.v. Injection of
$^{67}$Ga-Citrate or $^{123}$IUdR
--Gamma Camera Imaging--

|  | n | 1 h | 3 h | 24 h |
|---|---|---|---|---|
| $^{67}$Ga | 4 | 2.76 ± 0.18 | 3.61 ± 0.15 | 5.09 ± 0.44 |
| $^{123}$IUdR | 4 | 4.13 ± 1.06 | 3.33 ± 0.92 | 3.07 ± 0.930 |

Injected dose: 0.2 mCi/rat $^{67}$Ga;
1.5 mCi/rat $^{123}$IUdR; i.v.
Injection volume: 0.1 ml
Data Analysis Equation: T/B Ratio = $A_t/A_b$
Where $A_t$ = counts in ROI (3 × 4) over pus capsule
$A_b$ = counts in ROI (3 × 4) over contralateral muscle 4. Pus capsule to contralateral tissue (T/B) ratios calculated from imaging of rats with bacterial infection and injected with gallium-67 citrate or $^{123}$IUdR (Table 6) demonstrate that the latter is superior to gallium-67 for the radioscintigraphic detection of these lesions at all the three time periods tested (1 h, 3 hrs, and 24 hrs):

TABLE 6

Pus Capsule to Contralateral Tissue (T/B)
Ratios (mean +SD) in Rats with Bacterial
Infection Following i.v. Injection of
$^{67}$Ga-citrate or $^{123}$IUdR
--Gamma Camera Imaging--

|  | n | 1 h | 3 h | 24 h |
|---|---|---|---|---|

TABLE 6-continued

Pus Capsule to Contralateral Tissue (T/B)
Ratios (mean +SD) in Rats with Bacterial
Infection Following i.v. Injection of
$^{67}$Ga-citrate or $^{123}$IUdR
--Gamma Camera Imaging--

| $^{67}$Ga | 3 | 1.26 ± 0.09 | 2.01 ± 0.24 | 1.91 ± 0.15 |
| $^{123}$IUdR | 4 | 3.72 ± 1.06 | 3.53 ± 0.80 | 5.35 ± 2.37 |

Injected dose: 0.2 mCi/rat $^{67}$Ga;
1.5 mCi/rat $^{123}$IUdR; i.v.
Injection volume: 0.1 ml
Data Analysis Equation: T/B Ratio = $A_t/A_b$
Where $A_t$ = counts in ROI (3 × 4) over pus capsule
$A_b$ = counts in ROI (3 × 4) over contralateral muscle

EXAMPLE 5

Total Photon Efficiencies of Radiopharmaceuticals

For use in calculating dosages, the relative photon efficiencies of $^{123}$IUdR and of gallium-67 were determined. As shown in Table 7, the total photon efficiency of $^{123}$I is about 1.2 times that of gallium-67.

TABLE 7

Total Photon Efficiency of Gamma Camera
With Respect to $^{123}$IUdR and gallium-67

|  | keV* | Frequency X | Camera Efficiency | = Total Photon Efficiency |
|---|---|---|---|---|
| $^{67}$Ga |  |  |  |  |
|  | 91.3 | 0.0296 | 1.0 | 0.0296 |
|  | 93.3 | 0.37 | 1.0 | 0.37 |
|  | 184.6 | 0.204 | 0.65 | 0.1326 |
|  | 209 | 0.0233 | 0.65 | 0.01515 |
|  | 300.2 | 0.166 | 0.25 | 0.0415 |
|  |  |  |  | 0.59 |
| $^{123}$I |  |  |  |  |
|  | 159 | 0.833 | 0.85 | 0.708 |

Hence, $^{123}$Iodine emits 159 keV gamma photons which are ideal for external imaging. In addition, the whole body effective dose of intravenously administered $^{123}$I-iodine (thyroid blocked) in adult man is 0.0481 rad/mCi, while that of gallium-67 citrate is 0.44 rad/mCi (Radiation dose to patients from radiopharmaceuticals. Annals of the ICRP, Vol.18, No.1–4, pages 142 and 263, 1987. Pergamon Press, Oxford, N.Y.). These values imply that the dose to an animal from the decay of $^{123}$I and gallium-67 would be the same when the radioactive $^{123}$I dose administered is about 9 times that of gallium-67. Since intravenously administered radioiodinated IUdR is dehalogenated rapidly in animals and man ($T_{1/2}$=5–7 min), the effective dose values for $^{123}$-iodide can be utilized for $^{123}$IUdR. Consequently, these approximations indicate that the injection of 10–15 mCi of $^{123}$IUdR should lead to an adsorbed dose equivalent to currently administered $^{67}$Ga-citrate doses (1–1.5 mCi/patient). Further, the photon efficiency of 123, is about 1.2 times that of gallium-67.

The invention having been fully described, modifications of the invention will become apparent to those of skill in the art. Such modifications are within the scope of the invention, which is defined by the claims set forth below.

What is claimed is:

1. A method for detection of inflammation in a mammal comprising:
   (a) identifying a mammal suspected of having an inflammation;
   (b) administering to the mammal by intravenous or intra-arterial injection a diagnostically effective dosage of a radiopharmaceutical agent consisting of a deoxyribonucleoside or deoxyribonucleotide labeled with a radioisotope of iodine, bromine, carbon, nitrogen, or oxygen; and
   (c) detecting an accumulation of radioactivity in a site in the mammal, said accumulation being an indication that inflammation is present in the site.

2. The method according to claim 1 wherein the radioisotope is a gamma emitter.

3. The method according to claim 1 wherein the radioisotope is a positron emitter.

4. The method according to claim 1 wherein the radioisotope is selected from the group consisting of iodine-122, iodine-123, iodine-124, iodine-125, iodine-126, iodine-131, bromine-75, bromine-76, bromine-77, bromine-80, bromine-80m, bromine-82, carbon-11, nitrogen-13, oxygen-14, and oxygen-15.

5. The method according to claim 1 wherein the deoxyribonucleoside or deoxyribonucleotide is a pyrimidine.

6. The method according to claim 5 wherein the pyrimidine is BUdR, IUdR, TdR, or CdR, or a monophosphate, diphosphate, or triphosphate derivative thereof.

7. The method according to claim 6, wherein the radioisotope is selected from the group consisting of iodine-122, iodine-123, iodine-124, iodine-125, iodine-126, iodine-131, bromine-75, bromine-76, bromine-77, bromine-80, bromine-80m, bromine-82, carbon-11, nitrogen-13, oxygen-14, and oxygen-15.

8. The method according to claim 7, wherein the pyrimidine is IUdR and the radioisotope is selected from the group consisting of iodine-122, iodine-123, iodine-124, iodine-125, iodine-126, and iodine-131.

9. The method according to claim 7, wherein the pyrimidine is IUdR and the radioisotope is selected from the group consisting of carbon-11, nitrogen-13, oxygen-14, and oxygen-15.

10. The method according to claim 7, wherein the pyrimidine is BUdR and the radioisotope is selected from the group consisting of bromine-75, bromine-76, bromine-77, bromine-80, bromine-80m, bromine-82, carbon-11, nitrogen-13, oxygen-14, and oxygen-15.

11. The method according to claim 2, wherein the diagnostically effective dosage is between about 0.5 mCi and about 500 mCi.

12. The method according to claim 3, wherein the diagnostically effective dosage is between about 0.5 mCi and about 30 mCi.

13. The method according to claim 1 wherein
   (a) the deoxyribonucleoside or deoxyribonucleotide is a purine, and
   (b) the radioisotope is a radioisotope of carbon, nitrogen, or oxygen.

14. The method according to claim 13 wherein
   (a) the purine is AdR or GdR, or a monophosphate, diphosphate, or triphosphate derivative thereof; and
   (b) the radioisotope is carbon-11, nitrogen-13, oxygen-14, or oxygen-15.

15. The method according to claim 1 wherein the radiopharmaceutical agent is a deoxyribonucleoside labeled with a radioisotope of iodine, bromine, carbon, nitrogen, or oxygen.

16. The method according to claim 1 wherein the inflammation is a sterile inflammation.

17. The method according to claim 1 wherein the inflammation is associated with a bacterial infection.

18. The method according to claim 1 wherein the detecting step is carried out using a gamma camera, positron emission tomography (PET), or single photon emission computed tomography (SPECT).

19. An article of manufacture for use in detecting and localizing inflammation in a host comprising:
   (a) a sterile vial;
   (b) contained within the vial, a radiopharmaceutical agent in a pharmaceutically acceptable carrier, the agent being a deoxyribonucleoside or deoxyribonucleotide labeled with a radioisotope of iodine, bromine, carbon, nitrogen, or oxygen; and
   (c) instructions for using the agent in detecting and localizing inflammation in a host via intravenous or intra-arterial injection into the host.

20. A method for detection of inflammation in a mammal comprising:
   (a) identifying a mammal suspected of having an inflammation;
   (b) administering to the mammal by intraperitoneal or intrathecal injection a diagnostically effective dosage of a radiopharmaceutical agent consisting of a deoxyribonucleoside or deoxyribonucleotide labeled with a radioisotope of iodine, bromine, carbon, nitrogen, or oxygen; and
   (c) detecting an accumulation of radioactivity in a site in the mammal, said accumulation being an indication that inflammation is present in the site.

21. The method according to claim 20 wherein the radioisotope is a gamma emitter.

22. The method according to claim 20 wherein the radioisotope is a positron emitter.

23. The method according to claim 20 wherein the radioisotope is selected from the group consisting of iodine-122, iodine-123, iodine-124, iodine-125, iodine-126, iodine-131, bromine-75, bromine-76, bromine-77, bromine-80, bromine-80m, bromine-82, carbon-11, nitrogen-13, oxygen-14, and oxygen-15.

24. The method according to claim 20 wherein the deoxyribonucleoside or deoxyribonucleotide is a pyrimidine.

25. The method according to claim 24 wherein the pyrimidine is BUdR, IUdR, TdR, or CdR, or a monophosphate, diphosphate, or triphosphate derivative thereof.

26. The method according to claim 25, wherein the radioisotope is selected from the group consisting of iodine-122, iodine-123, iodine-124, iodine-125, iodine-126, iodine-131, bromine-75, bromine-76, bromine-77, bromine-80, bromine-80m, bromine-82, carbon-11, nitrogen-13, oxygen-14, and oxygen-15.

27. The method according to claim 26, wherein the pyrimidine is IUdR and the radioisotope is selected from the group consisting of iodine-122, iodine-123, iodine-124, iodine-125, iodine-126, and iodine-131.

28. The method according to claim 26, wherein the pyrimidine is IUdR and the radioisotope is selected from the group consisting of carbon-11, nitrogen-13, oxygen-14, and oxygen-15.

29. The method according to claim 26, wherein the pyrimidine is BUdR and the radioisotope is selected from the group consisting of bromine-75, bromine-76, bromine-77, bromine-80, bromine-80m, bromine-82, carbon-11, nitrogen-13, oxygen-14, and oxygen-15.

30. The method according to claim 21, wherein the diagnostically effective dosage is between about 0.5 mCi and about 500 mCi.

31. The method according to claim 22, wherein the diagnostically effective dosage is between about 0.5 mCi and about 30 mCi.

32. The method according to claim 20 wherein
   (a) the deoxyribonucleoside or deoxyribonucleotide is a purine, and
   (b) the radioisotope is a radioisotope of carbon, nitrogen, or oxygen.

33. The method according to claim 32 wherein
   (a) the purine is AdR or GdR, or a monophosphate, diphosphate, or triphosphate derivative thereof; and
   (b) the radioisotope is carbon-11, nitrogen-13, oxygen-14, or oxygen-15.

34. The method according to claim 20 wherein the radiopharmaceutical agent is a deoxyribonucleoside labeled with a radioisotope of iodine, bromine, carbon, nitrogen, or oxygen.

35. The method according to claim 20 wherein the inflammation is a sterile inflammation.

36. The method according to claim 20 wherein the inflammation is associated with a bacterial infection.

37. The method according to claim 20 wherein the detecting step is carried out using a gamma camera, positron emission tomography (PET), or single photon emission computed tomography (SPECT).

38. An article of manufacture for use in detecting and localizing inflammation in a host comprising:
   (a) a sterile vial;
   (b) contained within the vial, a radiopharmaceutical agent in a pharmaceutically acceptable carrier; the agent being a deoxyribonucleoside or deoxyribonucleotide labeled with a radioisotope of iodine, bromine, carbon, nitrogen, or oxygen; and
   (c) instructions for using the agent in detecting and localizing inflammation in a host via intraperitoneal or intrathecal injection.

* * * * *

UNITED STATES PATENT AND TRADEMARK OFFICE
CERTIFICATE OF CORRECTION

PATENT NO. : 5,811,073
APPLICATION NO. : 08/492425
DATED : September 22, 1998
INVENTOR(S) : Kassis et al.

It is certified that error appears in the above-identified patent and that said Letters Patent is hereby corrected as shown below:

In the Specification

At Column 1, Line number 8, please delete the paragraph and replace it with the following:
This invention was made with government support under CA015523 awarded by the National Institutes of Health. The government has certain rights in the invention.

Signed and Sealed this
Seventeenth Day of December, 2024

Derrick Brent
*Acting Director of the United States Patent and Trademark Office*